United States Patent [19]

Wu

[11] 4,328,372

[45] May 4, 1982

[54] RECOVERY OF CYCLOHEXANONE FROM CYCLOHEXYLBENZENE HYDROPEROXIDE ACID CLEAVAGE PRODUCT

[75] Inventor: Yulin Wu, Bartlesville, Okla.

[73] Assignee: Phillips Petroleum Company, Bartlesville, Okla.

[21] Appl. No.: 52,534

[22] Filed: Jun. 27, 1979

[51] Int. Cl.³ ............................................. C07C 45/53
[52] U.S. Cl. ................................... 568/361; 568/366; 568/376; 568/754
[58] Field of Search .................... 260/586 R; 568/366, 568/361, 376, 366; 578/754

[56] References Cited

U.S. PATENT DOCUMENTS 2,974,174  3/1961  Edmiston ............................ 568/366
3,316,302  4/1967  Steeman et al. .................... 568/366

Primary Examiner—Paul J. Killos

[57] ABSTRACT

Ketal and hemiketal found in the reaction mass resulting from the acid catalyzed cleavage of cyclohexylbenzene hydroperoxide in the presence of alcohol are removed from the reaction mass resulting upon the acid catalyzed cleavage by separating an organic layer from said mass and treating said organic layer with an acid thus improving the yield of cyclohexanone, recovering alcohol and facilitating ensuing purification operations.

10 Claims, No Drawings

RECOVERY OF CYCLOHEXANONE FROM CYCLOHEXYLBENZENE HYDROPEROXIDE ACID CLEAVAGE PRODUCT

BRIEF SUMMARY OF THE INVENTION

Improved yield of cyclohexanone in the acid catalyzed cleavage of cyclohexylbenzene hydroperoxide, in presence of an alcohol, is effected by acid-treating an organic layer recovered from the acid-cleavage product mixture. This forms cyclohexanone and regenerates the alcohol. Apparently, at least one of a ketal and a hemiketal of cyclohexanone is formed by reaction of the alcohol during the acid catalyzed cleavage operation.

DETAILED DESCRIPTION

This invention relates to the production of cyclohexanone. In one of its aspects, the invention relates to the improved production of cyclohexanone when cyclohexylbenzene hydroperoxide is converted to phenol and cyclohexanone in the presence of water, an alcohol, and an acid. In a more specific aspect, the invention relates to a treatment of an organic layer separated from the acid catalyzed cleavage product mass.

In one of its concepts, the invention provides a process for the improved recovery of cyclohexanone and recovery of alcohol which comprises treating an organic layer obtained from the acid catalyzed cleavage reaction mass obtained when cyclohexylbenzene hydroperoxide has been converted by acid cleavage to form cyclohexanone and phenol with an acid to cause conversion of at least one of a ketal and a hemiketal of cyclohexanone to cyclohexanone and corresponding alcohol. The conversion of cyclohexylbenzene to phenol and cyclohexanone by way of cyclohexylbenzene hydroperoxide is a well-known reaction. It has been found previously that the use of water, an alcohol, and an acid for the acid catalyzed cleavage of cyclohexylbenzene hydroperoxide to cyclohexanone and phenol is advantageous.

Apparently, it has not been recognized that during the acid catalyzed cleavage step, the alcohol and the cyclohexanone product react to form a ketal and a hemiketal.

The formation of the ketal and hemiketal not only causes the loss of a portion of one of the desired products (cyclohexanone), but also makes the purification of the product mixture more difficult. Thus, if the ketal and hemiketal can be and are removed the purification of the product mixture is considerably improved and thus, too, will yield an increased recovery of cyclohexanone. The present invention provides a process for converting the ketal and hemiketal to cyclohexanone and an alcohol, to recover the cyclohexanone product and to simplify the separation of the reaction mixture components.

According to the invention, the acid cleavage product mixture is separated into two layers and the organic layer is treated with an aqueous acid solution to hydrolyze the ketal and hemiketal to cyclohexanone and an alcohol.

It is desirable to have a process for improving the yield of cyclohexanone in the overall process of the acid catalyzed cleavage of cyclohexylbenzene hydroperoxide.

It is an object of this invention to produce cyclohexanone. It is another object of the invention to produce phenol and cyclohexanone. A further object of the invention is to provide a process for the recovery of cyclohexanone upon the acid catalyzed cleavage of cyclohexylbenzene hydroperoxide in the presence of water, alcohol, and the acid. It is a further object of the invention to generate cyclohexanone and alcohol from at least one of a ketal and a hemiketal which are present in the reaction mass obtained upon the acid catalyzed cleavage of cyclohexylbenzene hydroperoxide.

Other aspects, concepts, objects and the several advantages of the invention are apparent from a study of the disclosure and the appended claims.

According to the present invention, there is provided a process for converting at least one of a ketal and a hemiketal present in the reaction mass obtained upon the acid catalyzed cleavage of cyclohexylbenzene hydroperoxide in the presence of water, an alcohol, and an acid which comprises separating an organic layer from said mass and treating said layer with an aqueous acid solution under conditions to hydrolyze the ketal and hemiketal to form cyclohexanone and alcohol.

The involved reactions are illustrated by the following equations, using methanol.

The acid catalyzed cleavage of cyclohexylbenzene hydroperoxide (I) results in the production of phenol (II) and cyclohexanone (III).

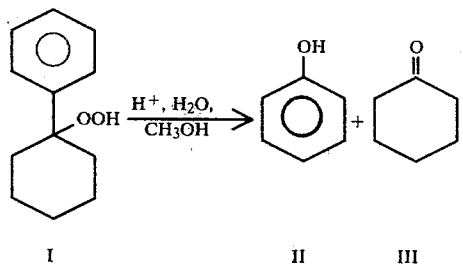

I    II    III

In the presence of the acid catalyst, cyclohexanone (III) reacts with methanol to yield the dimethyl ketal of cyclohexanone (IV) and the methyl hemiketal of cyclohexanone (V).

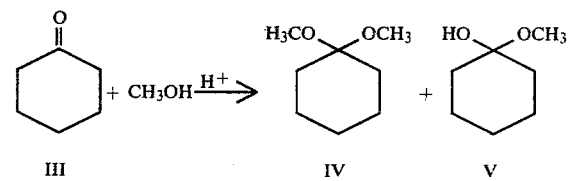

III    IV    V

In the process of the present invention, IV and V are treated with an aqueous acid to hydrolyze the ketal and hemiketal to yield cyclohexanone (III) and methanol.

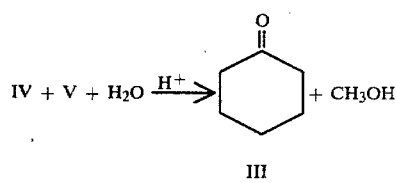

III

The above equations are not intended to show the stoichiometric relationships.

U.S. Pat. No. 4,021,490 issued May 3, 1977, Paul S. Hudson, discloses a process in which, among other steps, phenol and cyclohexanone are produced from cyclohexylbenzene hydroperoxide. The disclosure of the patent is incorporated herein by this reference. U.S. Pat. No. 3,405,038 issued Oct. 8, 1968, discloses the treatment of a hydroperoxide cleavage product with a water wash to remove the acid catalyst. British Pat. No. 629,429 discloses the acid catalyzed cleavage of hydroperoxides in the presence of alcohol and the water washing of the organic layer to remove residual acid. The disclosure of these patents is incorporated by this reference.

The process of the instant invention is applicable to mixtures resulting from the acid catalyzed cleavage of cyclohexylbenzene hydroperoxide. The cyclohexylbenzene hydroperoxide can be prepared by oxidation of cyclohexylbenzene using methods well-known in the art. The oxidation of cyclohexylbenzene is preferably carried out by contacting cyclohexylbenzene with oxygen at elevated temperatures. The usually employed range for the oxidation temperature is about 60° to about 160° C. This oxidation results in a mixture of cyclohexylbenzene and cyclohexylbenzene hydroperoxide. The cyclohexylbenzene can be prepared by any suitable method, but is preferably prepared by the hydroalkylation of benzene.

The acid catalyzed cleavage of cyclohexylbenzene hydroperoxide is carried out in a mixture of water, an acid, an alcohol, cyclohexylbenzene, and cyclohexylbenzene hydroperoxide.

Water utilized in the cleavage reaction will generally be in the range from about 0.1 to about 70 weight percent, and preferably will be in the range of about 0.5 to about 50 weight percent with the percentage being based on the weight of the total cleavage mixture.

The acid catalyst utilized in the hydroperoxide cleavage is a strong acid. Examples of suitable strong acids include mineral acids, such as sulfuric acid, hydrochloric acid, and nitric acid, or sulfonic acids such as p-toluenesulfonic acid, benzenesulfonic acid, and methanesulfonic acid. The amount of acid present in the mixture will be in the range of about 0.1 to about 60 weight percent and preferably about 1 to about 40 weight percent with the percentage being based on the weight of the total cleavage mixture.

The alcohol utilized in the cleavage reaction contains up to about 10 carbon atoms per molecule and can be represented by the following formula:

ROH wherein R is an alkyl radical containing from 1 to about 10 carbon atoms per radical, preferably from 1 to about 3 carbon atoms per radical. Examples of suitable alcohols include methanol, ethanol, 1-propanol, 2-propanol, 1-octanol, and the like. The currently preferred alcohol is methanol. The alcohol is present in the cleavage mixture in amounts in the range of about 0.1 to about 70 weight percent, preferably from about 1 to about 50 weight percent with the percentage being based on the total cleavage mixture weight.

Cyclohexylbenzene is generally present in amounts of about 5 to about 80 weight percent, preferably from about 10 to about 60 weight percent. Cyclohexylbenzene hydroperoxide will generally be present in amounts of about 0.5 to about 40 weight percent and preferably from about 1 to about 20 weight percent. All percentages are based on the weight of the total cleavage mixture.

The acid catalyzed cleavage of cyclohexylbenzene hydroperoxide is generally carried out in a temperature range of about 0° to about 90° C., preferably in a range of about 20° to about 70° C. The time required for the reaction will depend on the temperature and acid concentration chosen, but will generally be in the range from about 1 minute to about 24 hours, preferably from about 1 to about 5 hours.

Since efficient cleavage will be aided by intimate contact of the hydroperoxide and acid catalyst, good mixing will be of benefit and conventional methods of achieving good agitation can be employed as taught in the prior art.

Reaction vessels utilized in the cleavage reaction should be resistant to the acidic conditions. Suitable materials include glass and Inconel.

At the conclusion of the acid catalyzed hydroperoxide cleavage reaction, the mixture is cooled and two layers form. The two layers are separated and the aqueous layer (generally the bottom layer) can be recycled to the cleavage reaction zone if desired since it contains most of the alcohol and acid.

The organic layer (generally the top layer) contains phenol, cyclohexanone, cyclohexylbenzene, cyclohexanone ketal, cyclohexanone hemiketal, traces of water, the alcohol, and the acid. This organic layer is acid treated.

The acid treatment step of this invention is carried out by contacting the organic phase from the acid cleavage step with an aqueous acid under suitable conditions to hydrolyze a substantial amount of the cyclohexanone ketal and cyclohexanone hemiketal to cyclohexanone and an alcohol. The acid treatment can be carried out using any suitable method of contacting the organic phase and the aqueous acid. The aqueous acid generally will be contacted with the organic phase in a liquid-liquid contacting process. For example, various known extraction techniques such as batch or continuous operations using single or multistage contact or countercurrent extractions as described in Section 15 of Perry's "Chemical Engineers Handbook", 5th Edition, R. H. Perry and C. H. Chilton, McGraw-Hill Book Co., N.Y. (1973) can be utilized. Likewise, techniques for liquid-liquid contact and separation, which are described in Section 21 of said handbook can be utilized. In general it is advisable to use an apparatus resistant to acids.

The acid used in the acid treatment of this invention are those acids commonly considered to be "strong" acids. Examples of suitable strong acid catalysts include mineral acids, such as sulfuric acid, nitric acid, and hydrochloric acid, and sulfonic acids such as p-toluenesulfonic acid, benzenesulfonic acid, and methanesulfonic acid. It is advantageous to use the same acid in both the acid cleavage step and in the acid treatment step. Sulfuric acid is the presently preferred acid for use in both steps. The amount of acid in the aqueous acid used in the acid treatment will be broadly from about 0.01 to about 40 weight percent, preferably about 0.1 to about 20 weight percent with the percentage being based on the weight of the aqueous solution. The amount of aqueous acid utilized in the acid treatment can vary widely relative to the amount of the organic phase. In general, in a batch process the amount of the aqueous acid will be from about 1 to about 1000 weight percent and preferably will be from about 5 to about 500 weight percent with the percentage being based on the weight of the organic phase. As shown in the examples, the larger quantities of aqueous acid are of no particular advantage over the smaller quantities and for economic reasons lower levels of aqueous acid would generally be utilized. Multiple acid treatments can be utilized if desired.

The acid treatment can be carried out at any suitable temperature. Generally temperatures between about 0° and about 80° C. and preferably between about 10° and about 40° C. are utilized.

Because the acid treatment is carried out in the presence of two phases, it is expected that good mixing will be of benefit and conventional means of achieving good agitation and contact between the phases can be employed as taught in the prior art.

The amount of time employed in the acid treatment will depend on the temperature, acid concentration, and the type of apparatus. In general, the time will vary from a few minutes to several hours.

At the conclusion of the acid treatment the two phases are separated. The organic layer can be washed with water if desired or can be treated with a base to remove any residual acid. The organic mixture will normally be dried using any suitable means such as molecular sieves or calcium oxide. The dry organic mixture can then be separated by any suitable technique such as fractional distillation or extractive distillations as taught in, for example, U.S. Pat. Nos. 4,016,049, 4,019,965, 4,021,490, or 4,115,204 through 4,115,207.

The aqueous layer from the acid treatment can be recycled to the acid treatment zone. Since the acid treatment removes residual acid in the organic layer from the acid cleavage step, the acid content of the acid treatment solution generally increases during repeated recycles. When the acid content increases to an undesirably high level, the acid solution can either be diluted with water or used in the hydroperoxide acid cleavage step.

The products of the acid catalyzed cleavage of cyclohexylbenzene hydroperoxide are cyclohexanone and phenol. Both products are important industrial chemicals. Phenol is used as a disinfectant and as an intermediate in the preparation of a wide variety of medical and industrial organic compounds and dyes. Cyclohexanone is useful as an industrial solvent and as an intermediate in the preparation of adipic acid which is utilized in the production of polyamides such as nylon 6,6.

EXAMPLES

The cyclohexylbenzene (CHB) utilized in the following examples was prepared by the hydroalkylation of benzene by known methods. The cyclohexylbenzene was oxidized to cyclohexylbenzene hydroperoxide at 120° C. for a time period of about 5 hours in the presence of aqueous sodium hydroxide and an initiator (cyclohexylbenzene hydroperoxide).

The ketal and hemiketal formed from cyclohexanone and methanol during the acid catalyzed cleavage of cyclohexylbenzene hydroperoxide were identified by gas chromatographic-mass spectral analysis. The results given in the examples are gas liquid chromatography (glc) area percents and are not corrected for response factors.

EXAMPLE I

In a control run a 100 ml round bottom flask equipped with a magnetic stirrer and an addition funnel was charged with 6 g. methanol and 20 g. of a mixture containing 12 weight percent cyclohexylbenzene hydroperoxide in CHB with the percentage being based on the weight of the mixture. The reaction mixture was stirred at 50° C. and 2.06 g. of 70 percent sulfuric acid was added by the addition funnel over a 2 minute period. The mixture was stirred at 50° C. for 1.5 hours and then cooled. Two layers were formed in the reaction mixture and the layers were separated in a separatory funnel. The upper layer was analyzed by gas-liquid chromatography (glc). The upper layer was then washed with 10 ml water and analyzed by glc. The results of the two analyses are presented in Table I.

TABLE I

|  | Ketal and Hemiketal, % | Cyclohexanone, % | Phenol, % |
| --- | --- | --- | --- |
| Before Water Wash | 0.189 | 0.89 | 1.02 |
| After Water Wash | 0.156 | 1.22 | 0.90 |

The results in Table I show that a water wash of the hydroperoxide cleavage mixture hydrolyzes little of the ketal and hemiketal products.

EXAMPLE II

In an invention run, a 250 ml three necked round bottom flask equipped with a mechanical stirrer and an addition funnel was charged with 100 g. of a mixture of CHB and cyclohexylbenzene hydroperoxide. The mixture contained 15.62 weight percent cyclohexylbenzene hydroperoxide with the percentage being based on the total weight of the mixture. A mixture of 37 g. methanol and 12.3 g. of 70 weight percent sulfuric acid was added over a 3 minute time period from the addition funnel to the stirred, heated (60° C.) reaction mixture. The reaction mixture was stirred at 60° C. for 1.5 hours and then cooled. The cooled mixture formed two layers which were separated.

The lower layer (acidic solution) separated from the two layer reaction mixture contains water, methanol, sulfuric acid, and some phenol. The acidic solution was mixed with a mixture prepared from 1.65 g. methanol and 0.55 g. of 70% sulfuric acid to compensate for losses during the reaction and separation and was recycled to the addition funnel of the reaction vessel for the next reaction.

The upper layer separated from the two layer reaction mixture was not used further since the first cleavage and separation involved a methanol-water-sulfuric acid mixture that was not equilibrated with phenol and would not be representative of runs using recycled acid mixtures.

The reaction vessel was charged with 100 g. of the same CHB-cyclohexylbenzene hydroperoxide as described above. Another hydroperoxide cleavage run (run 1) was carried out as described above. The lower acidic layer was separated and a makeup mixture containing 1.65 g methanol and 0.55 g 70% sulfuric acid was added to said layer to render it suitable for use in the next reaction as previously described. The upper organic layer was treated with 0.7 g $CaCO_3$ for 30 minutes at room temperature with stirring and was then filtered. The filtrate was saved for later treatment.

Four more cleavage runs (runs 2-5) were carried out as described above for run 1 using for each run the recycled acid layer from the previous run. A 10 g. sample was taken from run 3 for use in Example III. The filtered organic layers from runs 1 through 5 were combined and analyzed by glc. Two 10 g. samples were taken from the combined cleavage product for two acid treatments.

In acid treatment A, a 10 g. sample of the cleavage product was treated with 1 g. of 10 weight percent sulfuric acid at room temperature in a separatory funnel, separated, and washed with 1 g. of water. The cleavage product was then treated with 0.1 g. of $CaCO_3$, filtered, and analyzed.

In acid treatment B, a 10 g. sample of the cleavage product was treated with 49 g. of 10 weight percent sulfuric acid at room temperature in a separatory funnel, separated, and washed with 20 g. of water. The cleavage product was then treated with 0.1 g of $CaCO_3$, filtered, and analyzed by glc. Table II presents the analyses of the cleavage product before and after the acid treatments.

TABLE II

|  | Ketal and Hemiketal % | Cyclohexanone, % | Phenol, % |
|---|---|---|---|
| Before Acid Treatment | 0.81 | 3.38 | 5.75 |
| After Acid Treatment A[a] | 0.05 | 3.87 | 5.06 |
| After Acid Treatment B[b] | 0.06 | 4.0 | 5.50 |

[a] 10 g. of cleavage product treated with 1 g. of 10 weight % $H_2SO_4$ and washed with 1 g. of $H_2O$.
[b] 10 g. of cleavage product treated with 49 g. of 10 weight % $H_2SO_4$ and washed with 20 g. of $H_2O$.

The results shown in Table II demonstrates operability of the process of this invention for the substantial decrease in levels of the ketal and hemiketal of cyclohexanone by the acid treatment of the cyclohexylbenzene hydroperoxide cleavage product. A comparison of these results with the results in Table I clearly shows the improvement in ketal and hemiketal removal by the acid treatment over a water wash.

EXAMPLE III

In another control run using a water wash instead of the acid treatment of the present invention, a 10 g. sample from run 3 in Example II was analyzed by glc, washed twice with 5 ml portions of water, treated with 0.1 g. of $CaCO_3$, filtered, and analyzed by glc. Table III shows the results of the analyses before and after the water washes.

TABLE III

|  | Ketal and Hemiketal % | Cyclohexanone, % | Phenol, % |
|---|---|---|---|
| Before Water Wash | 0.70 | 3.50 | 6.28 |
| After Water Wash[a] | 0.21 | 3.76 | 5.92 |

[a] 10 g. of cleavage product washed with two 5 ml portions of water.

The results presented in Table III show that two water washes of the cleavage mixture removes some of the ketal and hemiketal, but the water wash is much less effective than the acid treatments of the present invention as described in Example II.

Reasonable variation and modification are possible in the scope of the foregoing disclosure and the appended claims to the invention, the essence of which is that there have been found in the acid catalyzed cleavage reaction product obtained upon the acid catalyzed cleavage of cyclohexylbenzene hydroperoxide, a ketal and a hemiketal which can be and are removed by an acid treatment, as herein described, consequently increasing the recovery of cyclohexanone and alcohol upon the conversion of the ketal and hemiketal by said acid treatment.

I claim:

1. A process for the improved recovery of cyclohexanone and alkanol products from the acid catalyzed cleavage of cyclohexylbenzene hydroperoxide which comprises the steps of:
   (1) allowing the organic and aqueous phases to separate upon cooling of the reaction mass;
   (2) removing the organic phase; and
   (3) treating the organic phase with acid.

2. A process according to claim 1 wherein the acid is a strong acid.

3. A process according to claim 2 wherein the treatment is effected at a temperature in the range of from about 0° to about 80° C.

4. A process according to claim 1 wherein the alkanol is methanol, and the cleavage product contains the dimethyl ketal of cyclohexanone and the methyl hemiketal of cyclohexanone.

5. A process according to claim 1 wherein the acid for the acid treatment is the same acid used for the cleavage step.

6. A process according to claim 1 wherein the cyclohexylbenzene hydroperoxide acid catalyzed cleavage reaction mass has been obtained employing water, an alcohol, and an acid.

7. A process according to claim 6 wherein the acid treatment is effected at a temperature in the approximate range of from about 0° to about 80° C.

8. A process according to claim 7 wherein the alkanol is methanol and the cleavage reaction product contains the dimethyl ketal of cyclohexanone and the methyl hemiketal of cyclohexanone.

9. A process according to claim 8 wherein the acid for the acid treatment is the same acid used for the cleavage step.

10. A process for the improved recovery of cyclohexanone and alkanol from the acid catalyzed cleavage of cyclohexylbenzene hydroperoxide which comprises
    (1) permitting the aqueous and organic layers to separate upon cooling;
    (2) removing the organic phase; and
    (3) treating the organic phase with acid at a temperature of from about 0° to about 80° C.

* * * * *